(12) United States Patent
Takahashi

(10) Patent No.: US 11,360,020 B2
(45) Date of Patent: Jun. 14, 2022

(54) GAS ANALYSIS DEVICE, PROGRAM FOR GAS ANALYSIS DEVICE, AND GAS ANALYSIS METHOD

(71) Applicant: HORIBA, LTD., Kyoto (JP)

(72) Inventor: Motonobu Takahashi, Kyoto (JP)

(73) Assignee: HORIBA, LTD., Kyoto (JP)

( * ) Notice: Subject to any disclaimer, the term of this patent is extended or adjusted under 35 U.S.C. 154(b) by 313 days.

(21) Appl. No.: 16/492,358

(22) PCT Filed: Apr. 17, 2018

(86) PCT No.: PCT/JP2018/015803
§ 371 (c)(1),
(2) Date: Sep. 9, 2019

(87) PCT Pub. No.: WO2019/012773
PCT Pub. Date: Jan. 17, 2019

(65) Prior Publication Data
US 2021/0131955 A1 May 6, 2021

(30) Foreign Application Priority Data
Jul. 14, 2017 (JP) .............................. JP2017-138480

(51) Int. Cl.
*G01J 5/02* (2022.01)
*G01N 21/3504* (2014.01)
(Continued)

(52) U.S. Cl.
CPC ..... *G01N 21/3504* (2013.01); *G01N 33/0036* (2013.01); *G01N 2021/3595* (2013.01);
(Continued)

(58) Field of Classification Search
CPC ........... G01N 21/3504; G01N 33/0036; G01N 2021/3595; G01N 2201/0231; G01N 2201/127; G01N 21/61; G01N 21/274
See application file for complete search history.

(56) References Cited

U.S. PATENT DOCUMENTS 6,894,297 B1 5/2005 Inoue et al.
2012/0078532 A1* 3/2012 Forsyth ................ G01N 21/274
702/24

FOREIGN PATENT DOCUMENTS

JP 1995198600 A 8/1995
JP 2926277 B 7/1999
(Continued)

OTHER PUBLICATIONS

Slager et al., "Simple methods for calibrating IR in TGA/IR analyses", Thermochimica Acta, vol. 426, pp. 93-99. (Year: 2005).*
(Continued)

*Primary Examiner* — Kiho Kim
(74) *Attorney, Agent, or Firm* — Brooks Kushman P.C.

(57) ABSTRACT

In order to enable concentrations of components to be measured to be accurately calculated even when higher boiling compounds are contained in a test gas, a gas analysis device that analyzes components to be measured that are contained in a test gas using a light spectrum obtained by irradiating light onto the test gas is provided with a calibration curve data storage section in which is stored first calibration curve data in which effects on concentrations of the components to be measured from higher boiling compounds whose boiling point is higher than a heating temperature of an analyzer into which the test gas has been introduced have been corrected, and with a concentration calculation section that calculates concentrations of components to be measured using the first calibration curve data.

9 Claims, 6 Drawing Sheets

(51) Int. Cl.
*G01N 33/00* (2006.01)
*G01N 21/35* (2014.01)
(52) U.S. Cl.
CPC ............... *G01N 2201/0231* (2013.01); *G01N 2201/127* (2013.01)

(56) References Cited

FOREIGN PATENT DOCUMENTS

| JP | 2002-062288 A | 2/2002 |
|---|---|---|
| JP | 2003-050203 A | 2/2003 |
| JP | 2003-215037 A | 7/2003 |
| JP | 2004-101416 A | 4/2004 |
| JP | 2010-151624 A | 7/2010 |
| JP | 2013-130488 A | 7/2013 |
| JP | 2017194458 A | 10/2017 |

OTHER PUBLICATIONS

Decision to grant a patent dated May 6, 2021 issued for JP patent application No. 2019-529452.
International Search Report dated Jul. 10, 2018 issued for International Application No. PCT/JP/2018/015803.
EESR dated Feb. 23, 2021 issued in EP Patent Application No. 18831114.6, 8 pgs.

\* cited by examiner

GAS ANALYSIS DEVICE, PROGRAM FOR GAS ANALYSIS DEVICE, AND GAS ANALYSIS METHOD

CROSS-REFERENCE TO RELATED APPLICATION

This application is the U.S. national phase of PCT Application No. PCT/JP2018/015803, filed Apr. 17, 2018, Which claims priority to Japanese Patent Application No. 2017-138480, filed Jul. 14, 2017, which are both incorporated by reference herein in their entireties.

TECHNICAL FIELD

The present invention relates to a gas analysis device, a program for a gas analysis device, and a gas analysis method.

TECHNICAL BACKGROUND

As is shown in Patent Document 1, a conventional gas analysis device is known that employs, for example, Fourier transform infrared (FTIR) spectroscopy to calculate concentrations of components to be measured that are contained in a test gas by performing multivariate analysis using an absorption spectrum obtained by irradiating light onto the test gas.

Analysis performed using FTIR spectroscopy has the advantage of enabling multicomponent analysis of components contained in a test gas to be performed continuously and simultaneously. Additionally, if FTIR spectroscopy is used in, for example, the field of engine exhaust gas, then this is advantageous as it enables what is known as 'wet measurement' to be performed. In wet measurement, the exhaust gas that is serving as the test gas can be introduced directly into a sample cell and analyzed, and the concentrations of components to be measured can be calculated while moisture is still contained in the exhaust gas.

In the aforementioned analysis, calibration curve data showing relationships between an absorption spectrum and concentrations of components to be measured is used. This calibration curve data is prepared in advance for each component to be measured by stipulating a plurality of components to be measured that are assumed to be contained in the test gas, and then correcting the interference from these components to be measured.

Here, in wet measurement, if moisture or gas having a low boiling point is condensed inside a pipe through which the test gas is flowing, then because changes occur in the concentrations and the like of the components to be measured, the pipes and analyzers are heated and are then held, for example, at a predetermined heating temperature.

Because of this, it is thought that higher boiling compounds whose boiling point is higher than the heating temperature are not present in a gaseous state and are not contained in the test gas, so that calibration curve data in which the interference from higher boiling compounds has not been corrected is being used for conventional calibration curve data.

However, even if the temperature of the exhaust gas has been adjusted to the heating temperature, there are times when, although in minute quantities, higher boiling compounds are sometimes still contained in a test gas. In such cases, if concentrations are calculated using conventional calibration curve data in which the interference from these higher boiling compounds have not been corrected, then measurement errors occur.

DOCUMENTS OF THE PRIOR ART

Patent Documents

[Patent Document 1] Japanese Patent No. 2926277

DISCLOSURE OF THE INVENTION

Problems to be Solved by the Invention

The present invention was conceived in order to collectively solve all of the above-described problems, and it is a principal object thereof to enable concentrations of components to be measured to be accurately calculated even when higher boiling compounds are contained in a test gas.

Means for Solving the Problem

In other words, a gas analysis device according to the present invention is a gas analysis device that analyzes components to be measured that are contained in a test gas using a light spectrum obtained by irradiating light onto the test gas, and is provided with a calibration curve data storage unit in which is stored first calibration curve data in which effects on concentrations of the components to be measured from higher boiling compounds whose boiling point is higher than a heating temperature of an analyzer into which the test gas has been introduced have been corrected, and a concentration calculation section that calculates concentrations of components to be measured using the first calibration curve data.

If a gas analysis device formed in this manner is employed, then even if higher boiling compounds are contained in a test gas, because a concentration calculation section calculates concentrations of components to be measured using first calibration curve data in which effects on the concentrations of the components to be measured from higher boiling compounds have been corrected, the effects from these higher boiling compounds are reduced, and concentrations of components to be measured can be accurately calculated.

It is preferable for the calibration curve data storage unit to additionally store second calibration curve data in which the effects from the higher boiling point compounds have not been corrected, and when the higher boiling point compounds are not contained in the test gas, for the concentration calculation section to calculate concentrations of the components to be measured using the second calibration curve data.

If this type of structure is employed, then if higher boiling point compounds are not contained in the test gas, because the concentration calculation section calculates concentrations of components to be measured using the second calibration curve data in which the effects from higher boiling point compounds have not been corrected, concentrations can be calculated using accurate calibration curve data irrespective of whether or not higher boiling compounds are present.

In order to make it possible to automatically differentiate between when to use the first calibration curve data and when to use the second calibration curve data, it is preferable for the calibration curve data storage unit to store calibration curve data for higher boiling compounds that is used to calculate concentrations of the higher boiling compounds, and for there to be further provided a determination section that determines whether or not concentrations of the higher boiling compounds calculated by the concentration calculation section using the higher boiling compound calibration curve data are equal to or less than a predetermined threshold value, and when the concentrations of the higher boiling compounds are determined by the determination section to be equal to or less than the predetermined threshold value, for the concentration calculation section to calculate concentrations of the components to be measured using the second calibration curve data.

In order to enable the first calibration curve data to be used automatically when higher boiling compounds are contained in the test gas, it is preferable for there to be further provided a qualitative analysis data acceptance section that receives qualitative analysis data obtained as a result of qualitative analysis being performed on the test gas, and when the qualitative analysis data shows that the higher boiling compounds are contained in the test gas, for the concentration calculation section to calculate concentrations of the components to be measured using the first calibration curve data.

In order to enable concentrations of components to be measured to be accurately calculated even when a plurality of types of higher boiling compounds are contained in a test gas, when the qualitative analysis data shows that a plurality of types of the higher boiling compounds are contained in the test gas, it is preferable for the concentration calculation section to use calibration curve data in which the effects on the concentrations of the components to be measured from the plurality of types of higher boiling compounds have been corrected as the first calibration curve data.

An example of the higher boiling compounds is an alkane having a carbon number of not less than 10 and not more than 20.

A more specific embodiment of the present invention is characterized in being provided with a cell that contains the test gas, and a heating unit that heats the cell, wherein a temperature of the cell that is heated by the heating unit is the heating temperature.

Furthermore, a program for a gas analysis device according to the present invention is a program that is used in a gas analysis device that analyzes components to be measured that are contained in a test gas using a light spectrum obtained by irradiating light onto the test gas, and that causes a computer to perform functions of a calibration curve data storage unit in which is stored first calibration curve data in which effects on concentrations of the components to be measured from higher boiling compounds whose boiling point is higher than a heating temperature of an analyzer into which the test gas has been introduced have been corrected, and a concentration calculation section that calculates concentrations of the components to be measured using the first calibration curve data.

In addition, a gas analysis method according to the present invention is a method of analyzing components to be measured that are contained in a test gas using a light spectrum obtained by irradiating light onto the test gas, and is provided with a calibration curve data storage step in which first calibration curve data in which effects on concentrations of the components to be measured from higher boiling compounds whose boiling point is higher than a heating temperature of an analyzer into which the test gas has been introduced have been corrected is stored, and a concentration calculation step in which concentrations of components to be measured are calculated using the first calibration curve data.

According to this gas analysis system, program for a gas analysis device, and gas analysis method, the same type of actions and effects as those obtained from the above-described gas analysis device can be achieved.

Effects of the Invention

According to the present invention which is formed in the above-described manner, it is possible to reduce measurement errors that are due to the effects from higher boiling compounds, so that an improvement in analysis accuracy is achieved.

DESCRIPTION OF THE SYMBOLS

X ... Gas Analysis System
100 ... Gas Analysis Device
1 ... Analysis Unit
2 ... Information Processing Device
21 ... Calibration Curve Data Storage Unit
22 ... Concentration Calculation Unit
23 ... Determination Unit
24 ... Abnormal Value Detection Unit
25 ... Output Unit

BEST EMBODIMENTS FOR IMPLEMENTING THE INVENTION

Hereinafter, a first embodiment of a gas analysis system according to the present invention will be described with reference to the drawings.

Figure 1:
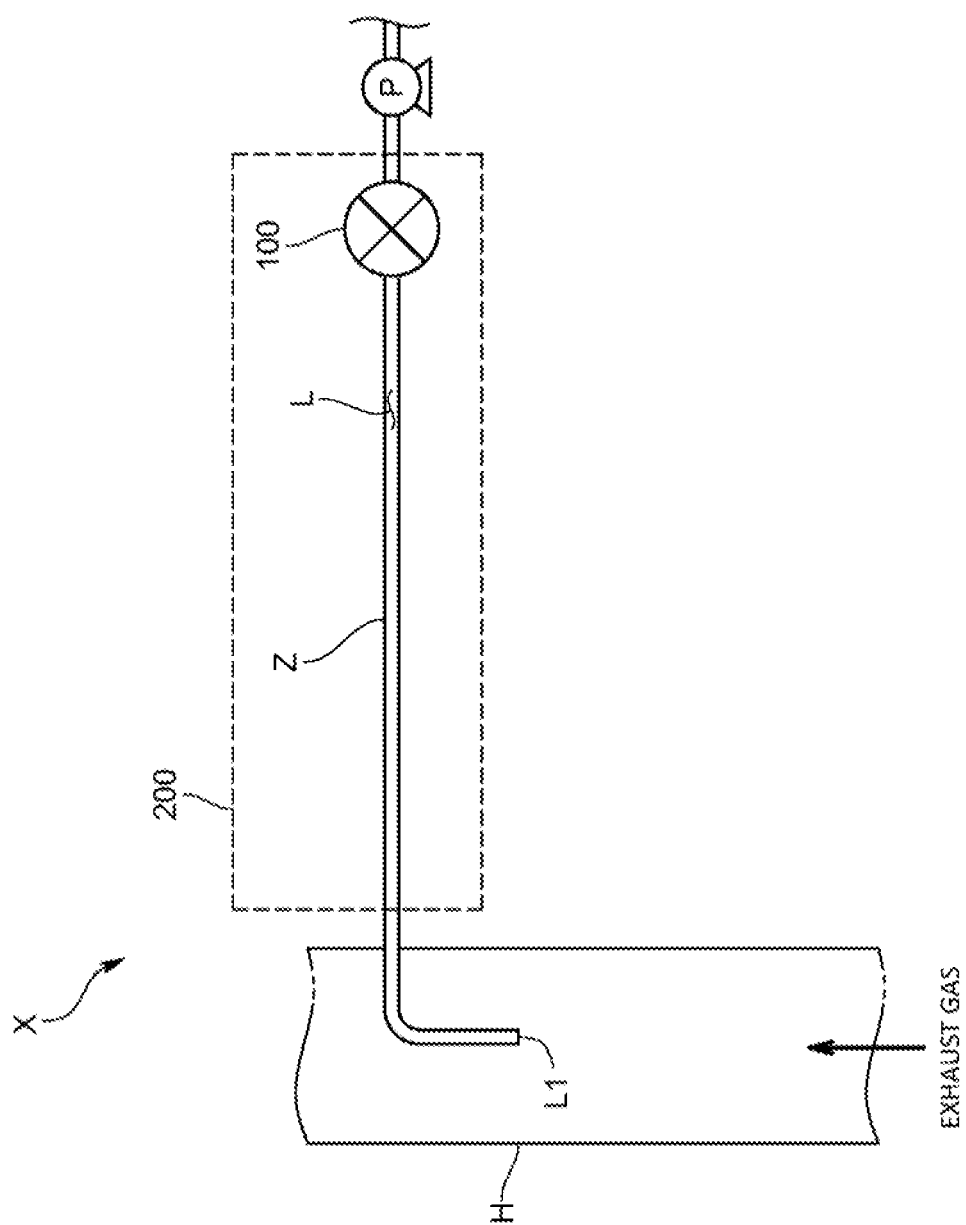
FIG. 1 is a schematic view showing a structure of a gas analysis system of a first embodiment.

A gas analysis system X of the present embodiment analyzes exhaust gas (i.e. test gas) emitted, for example, from an internal combustion engine such as an engine of an automobile or the like. More specifically, as is shown in FIG. 1, the gas analysis system X is equipped with a sampling line L that samples exhaust gas flowing through an exhaust pipe H, and a gas analysis device 100 that is provided on the sampling line L. Note that the gas analysis system X may also be used to analyze exhaust gas emitted from an internal combustion engine mounted in a moving body such as a ship or an airplane or the like.

The sampling line L is formed by a pipe Z having one end aperture L1 provided inside the exhaust pipe H, and directly samples exhaust gas flowing through the exhaust pipe H. The sampling line L additionally guides this exhaust gas to the gas analysis device 100 with the moisture component thereof still retained in the exhaust gas.

A heating unit 200 that heats the pipe Z to a predetermined heating temperature is provided in the pipe Z. More specifically, the heating unit 200 is provided with a coil shaped or circular-cylinder shaped heater that is provided on an outer surface of the pipe Z. and the exhaust gas flowing through the sampling line L is maintained at the heating temperature. Note that the heating temperature is a preset temperature (i.e., a set temperature) and may be, for example, 113° C. or 191° C. or the like.

Here, the heating unit 200 heats the gas analysis device 100, and then maintains the gas analysis device 100 at a preset heating temperature (i.e., set temperature) such as, for example, 113° C. or 191° C.

Figure 2:
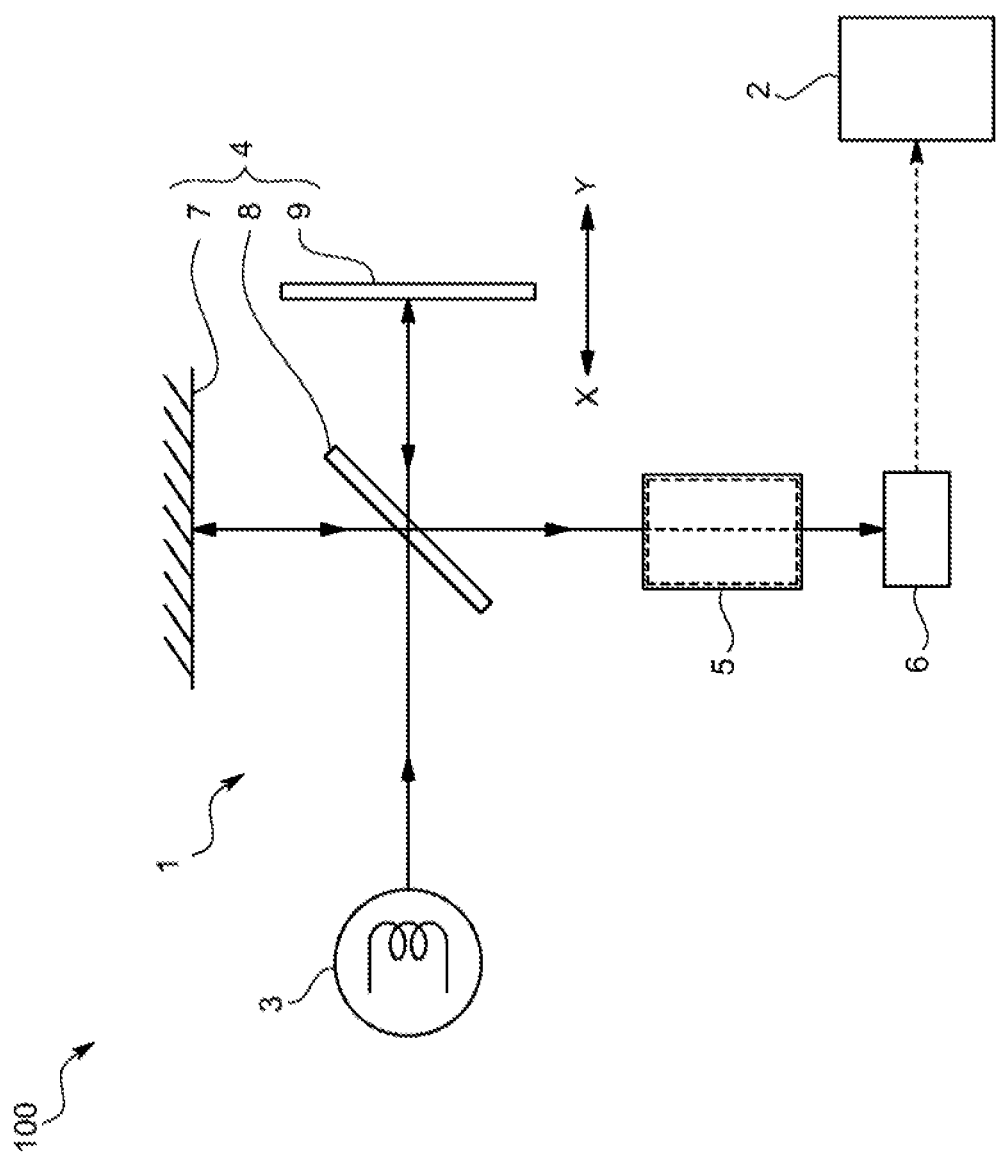
FIG. 2 is a schematic view showing a structure of a gas analysis device of the first embodiment.

The gas analysis device 100 measures concentrations of multiple components contained in a test gas by performing qualitative analysis on an absorption spectrum obtained by irradiating light onto the test gas. Here, the gas analysis device 100 continuously measures concentrations of multiple components contained in exhaust gas by using FTIR spectroscopy. More specifically, as is shown in FIG. 2, the gas analysis device 100 is provided with an analysis unit (i.e., an analyzer) 1 that outputs interferograms, and with an information processing device 2 that processes the interferograms that are output from the analysis unit 1.

The analysis unit 1 is provided with an infrared light source 3 that is formed so as to emit infrared light, an interference mechanism 4 that provides interference to the infrared light from the infrared light source 3 and outputs the resulting infrared light, a measurement cell 5 that contains exhaust gas, and onto which the infrared light from the infrared light source 3 is irradiated via the interference mechanism 4, and a light detector 6 that receives the infrared light that has passed through the measurement cell 5. The interference mechanism 4 is formed by a fixed mirror 7, a beam splitter 8, and a moving mirror 9 that is moved in parallel with, for example, an XY direction by a drive mechanism (not shown in the drawings).

Note that the above-described heating unit 200 heats the measurement cell 5 to a predetermined heating temperature.

The information processing device 2 is either a general purpose or a dedicated computer that is provided with a CPU, memory, input/output interfaces, an A/D converter, and the like. This computer is made to perform the functions of at least a calibration curve data storage unit 21 and a concentration calculation section 22 (see FIG. 3) as a result of the CPU and peripheral devices and the like being operated in mutual collaboration in accordance with a predetermined program stored in a predetermined area of the memory.

The calibration curve data storage unit 21 is used to store in advance for each component to be measured calibration curve data that is required to calculate concentrations of these components to be measured. The calibration curve data in this case is data in which interference on the concentrations of each component to be measured from the other components to be measured have been corrected, and is input in advance by a user via an input means.

In addition, the calibration curve data storage unit 21 of the present embodiment also stores calibration curve data (referred to below as 'first calibration curve data') in which the interference from higher boiling compounds have been corrected.

Higher boiling compounds are compounds whose boiling point is higher than the heating temperature of the analysis unit 1 into which the exhaust gas is introduced, more specifically, than the heating temperature of the measurement cell 5 (in other words, the temperature of the measurement cell 5 after this has been heated by the heating unit 200). In this case, the boiling point of these higher boiling compounds is higher than the heating temperature of the pipe Z through which the exhaust gas is flowing. More specifically, the boiling point of these higher boiling compounds is 113° C. or higher and is, for example, between approximately 180 and 350° C.

Specific examples of these higher boiling compounds include components contained in fuels such as light oil and gasoline and the like, and are compounds having a high carbon number that are generated as a result of the imperfect combustion of the aforementioned fuels. An example of a higher boiling compound is an alkane or the like having a high carbon number, and may be an alkane whose carbon number is, for example, not less than 10 and not more than 20 ($C_{10}$~$C_{20}$). These higher boiling compounds may include compounds whose boiling point is higher than the heating temperature of the catalyst when the performance of a catalyst provided inside the exhaust pipe H is being evaluated.

The first calibration curve data is prepared in advance by a user for each one of N types of components to be measured that are assumed to be contained in an exhaust gas, and either one or a plurality of higher boiling compounds are included in this N types of components to be measured.

If, for example, four components A, B, C, and D are contained in the exhaust gas, and of these, C and D are higher boiling compounds, then the first calibration curve data for A that is stored in the calibration curve data storage unit 21 is as follows.

First calibration curve data for A in which the interference from B. C, and D have been corrected First calibration curve data for A in which the interference from B and C have been corrected First calibration curve data for A in which the interference from B and D have been corrected First calibration curve data for A in which the interference from C and D have been corrected First calibration curve data for A in which the interference from C have been corrected First calibration curve data for A in which the interference from D have been corrected Note that first calibration curve data for B, C, and D is also stored in the calibration curve data storage unit 21 in the same way as the first calibration curve data for A.

In this way, first calibration curve data created for each individual combination of a plurality of types of higher boiling compounds is stored in the calibration curve data storage unit 21 of the present embodiment.

Moreover, the calibration curve data storage unit 21 of the present embodiment additionally stores calibration curve data in which the interference from higher boiling compounds have not been corrected (also described as 'second calibration curve data').

This second calibration curve data is prepared in advance for each component to be measured when the higher boiling compounds are excluded from the above-described N types of components to be measured.

If the aforementioned four components A, B, C, and D are considered, then the second calibration curve data that is stored in the calibration curve data storage unit 21 is as follows.

Second calibration curve data for A in which the interference from B have been corrected Second calibration curve data for B in which the interference from A have been corrected Second calibration curve data for A in which the interference from other components have not been corrected Second calibration curve data for B in which the interference from other components have not been corrected In this way, the calibration curve data storage unit 21 of the present embodiment stores calibration curve data in which the interference from every possible combination of N−1 (excluding itself) types of components to be measured on the N types component to be measured have been corrected, and if these are expressed using N, then Z types thereof are obtained as expressed by the following Formula (1).

$$Z = \sum_{k=1}^{N-1} ({}_N C_1 \times {}_{N-1} C_k) \qquad (1)$$

In Formula (1), the item ${}_N C_1$ shows which of the N types of components to be measured the calibration curve data belongs to, while the item ${}_{N-1} C_k$ shows the combinations of N−1 (excluding itself) types of components to be measured.

Furthermore, it is also possible for the calibration curve data for higher boiling compounds that is used to calculate the concentrations of the higher boiling compounds to be stored in advance in the calibration curve data storage unit 12. Here, data for higher boiling compounds corresponding to each of two components, namely, the above-described higher boiling compounds C and D is stored in the calibration curve data storage unit 12.

The concentration calculation section 22 receives interferograms output from the light detector 6 of the analysis unit 1, and also acquires calibration curve data stored in the calibration curve data storage unit 21 and then calculates the concentrations of each component to be measured.

More specifically, the concentration calculation section 22 firstly obtains a power spectrum by performing Fourier transform processing on each of an interferogram of a reference gas (for example, nitrogen gas) and an interferogram of exhaust gas, and then determines a ratio of the power spectrum of the exhaust gas relative to the power spectrum of the reference gas. This ratio is then converted into an absorbance scale, and the concentrations of components to be measured that are contained in the exhaust gas are calculated based on the absorbances at a plurality of wave number points in this absorption spectrum.

Figure 3:
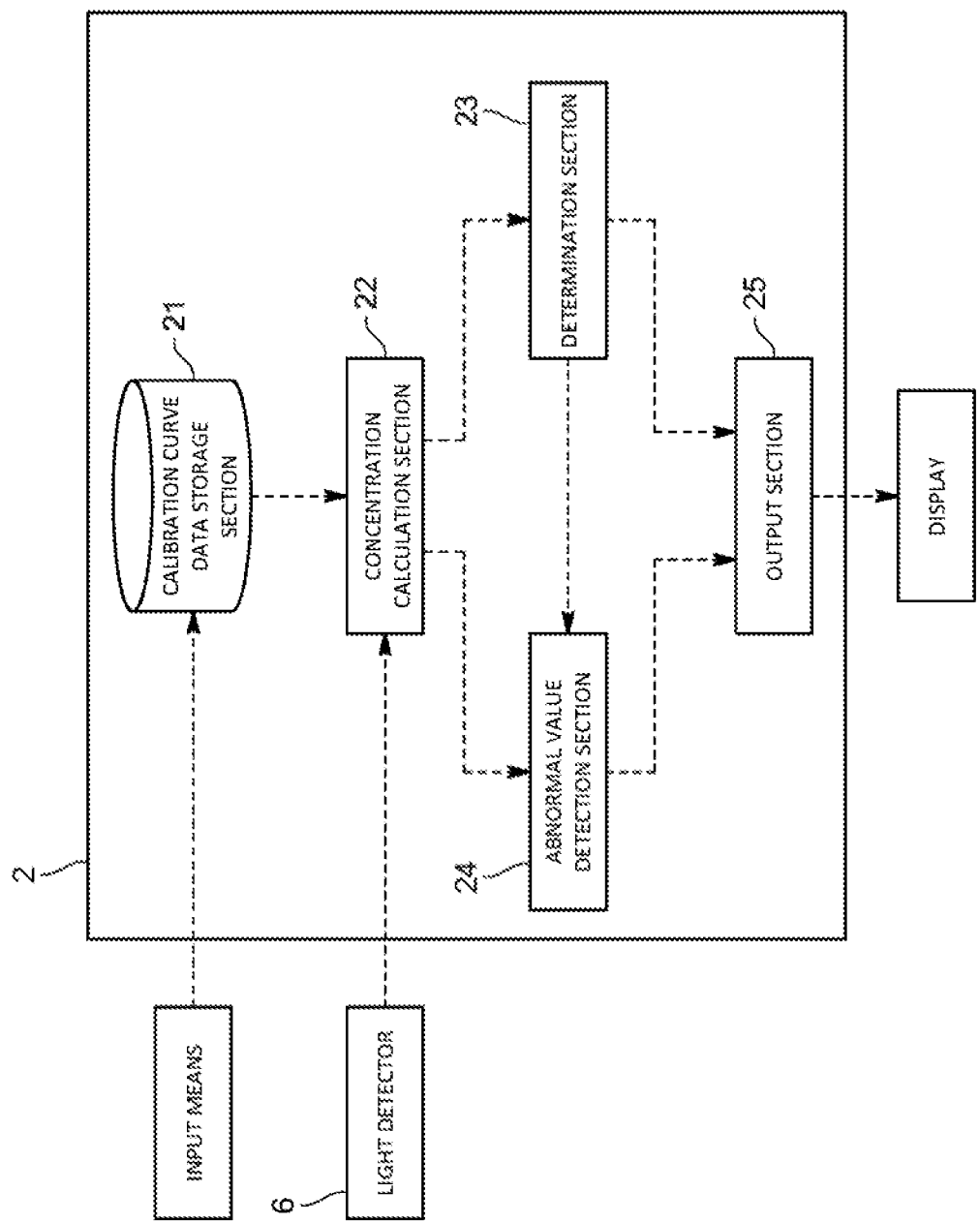
FIG. 3 is a function block diagram showing functions of an information processing device of the first embodiment.

Here, as is shown in FIG. 3, the information processing device 2 of the present embodiment is further provided with functions of a determination section 23, an abnormal value detection section 24, and an output section 25.

Figure 4:
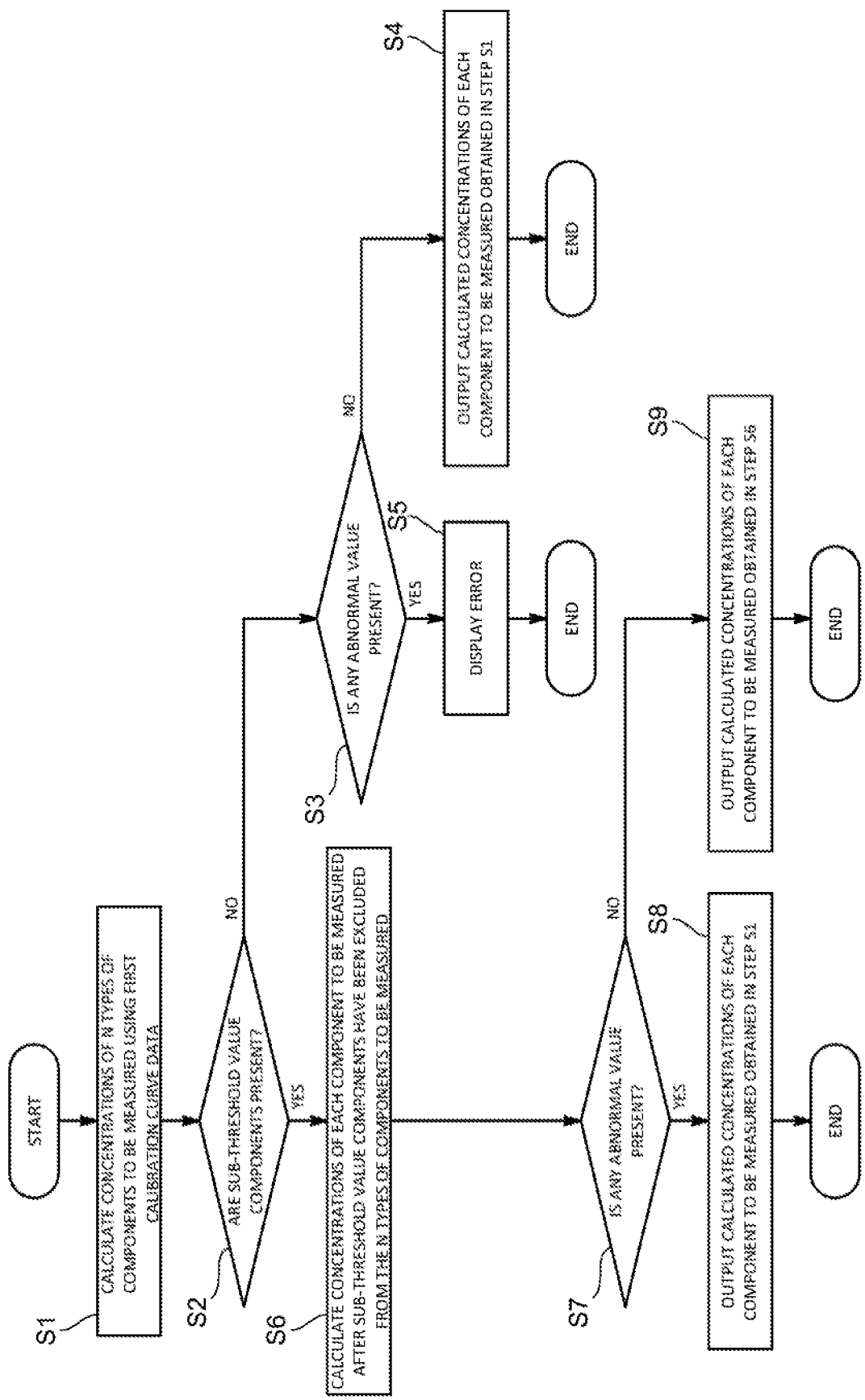
FIG. 4 is a flowchart showing an operation of the information processing device of the first embodiment.

Hereinafter, operations of the information processing device 2 of the present embodiment together with a description of each unit will be described with reference to the flowchart shown in FIG. 4.

When exhaust gas is guided to the analysis unit 1, firstly, the concentration calculation section 22 receives an interferogram output from the analysis unit 1, and acquires from the calibration curve data storage unit 21 the first calibration curve data which is required when all of the N types of components to be measured are contained in the exhaust gas, and then calculates concentrations of each of the N types of components to the measured (step S1). Calculated concentration data showing these calculated concentrations is then output to the determination section 23.

Next, the determination section 23 determines from the respective calculated concentrations of each of the components to be measured that are shown by the calculated concentration data whether or not any sub-threshold value components (i.e., components that are present in concentrations below a threshold value at which they can be regarded as being present) are present in the exhaust gas (step S2). More specifically, the determination section 23 compares the calculated concentrations of each component to be measured to a previously set threshold value, and components to be measured whose calculated concentration is less than the threshold value are detected as being sub-threshold value components.

If, in step S2, no sub-threshold value components are detected, a signal indicating this fact is output from the determination section 23 to the abnormal value detection section 24, and the calculated concentration data obtained in step S1 is output from the concentration calculation section 22 to the abnormal value detection section 24. When the abnormal value detection section 24 acquires the calculated concentration data obtained in step S1, it determines whether or not any abnormal values are contained in the calculated concentrations shown by this calculated concentration data (step S3).

More specifically, when a calculated concentration calculated by the concentration calculation section 22 is a value that it is not physically possible to generate, this calculated concentration is detected as being an abnormal value. Here, calculated concentrations that are obtained as negative values are detected as being abnormal values.

If no abnormal value is detected in step S3, then because N types of components to be measured are contained in the exhaust gas, the output section 25 acquires from the abnormal value detection section 24 the calculated concentration data obtained in step S1, and outputs calculated concentrations for each component to be measured, for example, to a display unit or the like (step S4).

If, on the other hand, an abnormal value is detected in step S3, for example, an error message is output on the display unit or the like (step S5).

If sub-threshold components are detected in step S2, the concentration calculation section 22 calculates the concentrations of the remaining components to be measured when these sub-threshold value components have been excluded from the N types of components to be measured (step S6).

At this time, if it is determined by the determination section 23 that a higher boiling compound is a sub-threshold value component, the concentration calculation section 22 acquires the second calibration curve data from the calibration curve data storage unit 21, and calculates concentrations of the components to be measured after the higher boiling compound has been excluded therefrom. Calculated concentration data showing these calculated concentrations is then output to the abnormal value detection section 24.

Here, if the sub-threshold value components excluded in step S6 are actually contained in the exhaust gas, the concentration calculation section 22 ends up calculating the concentrations of each component to be measured using calibration curve data in which the interference from these sub-threshold value components have not been corrected, so that the calculated concentrations obtained in step S6 may, for example, be negative values, or may be abnormally large values, or the like.

Therefore, when the abnormal value detection section 24 acquires the calculated concentration data obtained in step S6, it determines whether or not abnormal values are contained in the calculated concentrations shown by this calculated concentration data, in other words, are contained in the concentrations calculated by the concentration calculation section 22 in step S6 after the sub-threshold value components have been excluded therefrom (step S7).

More specifically, when a calculated concentration calculated by the concentration calculation section 22 is a value that it is not physically possible to generate, the abnormal value detection section 24 detects this calculated concentration as being an abnormal value. Here, calculated concentrations that result as negative values are detected as being abnormal values.

If an abnormal value is detected in step S7, then because there is a possibility that at least a portion of the sub-threshold value components excluded in step S6 are contained in the exhaust gas, the output section 25 acquires from memory (not shown in the drawings) where it is being temporarily stored the calculated concentration data obtained in the calculation performed by the concentration calculation section 22 immediately prior to the calculation performed in step S6, in other words, the calculated concentration data obtained in step S1, and outputs calculated concentrations for each component to be measured to a display unit or the like (step S8).

If, on the other hand, an abnormal value is not detected in step S7, then because this means that the remaining components to be measured after the sub-threshold value components have been excluded from the N types of components to be measured are contained in the exhaust gas, the output section 25 acquires the calculated concentration data obtained in step S6 from the abnormal value detection section 24, and outputs calculated concentrations for each component to be measured to a display unit or the like (step S9).

According to the exhaust gas analysis device 100 according to the present embodiment that is formed in the above-described manner, even if higher boiling compounds are contained in exhaust gas, because the concentration calculation section 22 firstly calculates concentrations of components to be measured using first calibration curve data in which the effects from the higher boiling compounds have been corrected, the interference from these higher boiling compounds are reduced, and concentrations of the components to be measured can be accurately calculated.

If higher boiling compounds are not contained in the exhaust gas, then because the concentration calculation section 22 calculates concentrations of components to be measured using the second calibration curve data in which the effects from the higher boiling compounds have not been corrected, it is possible to use highly accurate calibration curve data irrespective of whether or not higher boiling compounds are present.

Furthermore, because the calibration curve data storage unit 21 stores the respective calibration curve data for the N types of components to be measured, which is also calibration curve data in which the interference on all combinations of N−1 (excluding itself) types of components to be measured have been corrected, it is possible to calculate concentrations using the most appropriate calibration curve data that corresponds to the types of components to be measured that are contained in the exhaust gas.

In addition to this, if abnormal values are contained in the concentrations calculated by the concentration calculation section 22 after the sub-threshold value components have been excluded, because the abnormal value detection section 24 detects these abnormal values, then if such abnormal values are detected, it is possible to consider, for example, that there is a possibility that the components to be measured contained in the exhaust gas have actually been excluded as sub-threshold value components.

Note that the present invention is not limited to the above-described embodiment.

Figure 5:
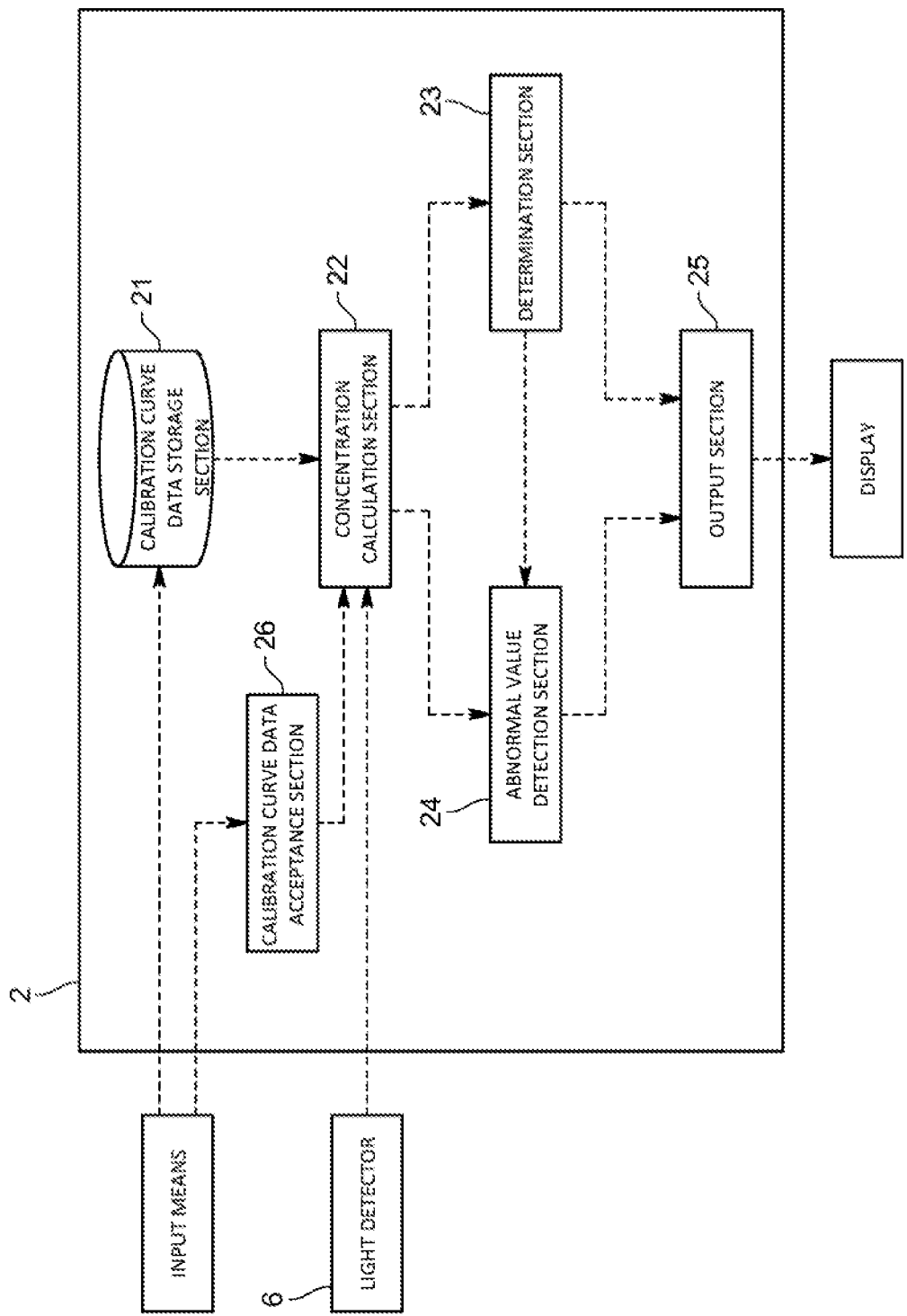
FIG. 5 is a function block diagram showing functions of an information processing device of a variant example of the first embodiment.

For example, in the above-described embodiment, the second calibration curve data is stored in advance in the calibration curve data storage unit 21, however, as is shown in FIG. 5, it is also possible for the information processing device 2 to be provided, for example, with a calibration curve data acceptance section 26 that receives second calibration curve data that has been input when necessary by a user.

If this type of structure is employed, if the first calibration curve data at least is stored in advance in the calibration curve data storage unit 21, then if higher boiling compounds are not contained in the exhaust gas, the user is able to create and input the second calibration curve data, and the calibration curve data acceptance section 26 is able to receive this second calibration curve data. As a consequence, a reduction in the memory capacity can be achieved, while concentrations can still be calculated using the second calibration curve data.

Note that is also possible to employ a structure in which the second calibration curve data is created automatically when necessary internally by the information processing device 2, and this second calibration curve data that is created is then received by the calibration curve data acceptance section 26.

In addition, in the above-described embodiment, the Z types of calibration curve data expressed by Formula (1) are stored in the calibration curve data storage unit 21, however, it is not absolutely essential that all of these Z types be stored, and it is also possible for just a portion of the Z types of calibration curve data to be stored.

In this case, if calibration curve data that has not been stored in the calibration curve data storage unit 21 is subsequently needed, then the aforementioned calibration curve data acceptance section is able to receive the calibration curve data input by a user via an input means, or the calibration curve data created internally by the information processing device 2.

Furthermore, in the above-described embodiment, the calibration curve data is data in which interference from other components on the components to be measured have been corrected, however, the calibration curve data may also be data in which coexistence effects from other components on the components to be measured have been corrected, or data in which both these interference and coexistence effects have been corrected. In other words, the term 'effects' referred to in the Claims is a concept that includes interference, coexistence effects, and both of these types of effects together.

In addition, mutually different calibration curve data may be used when the concentration of those components that have an effect on the concentrations of the components to be measured is low, and when the concentration of those components that have an effect on the concentrations of the components to be measured is high.

In addition, in the above-described embodiment, a gas analysis device 100 employing FTIR spectroscopy for analyzing automobile exhaust gas is described, however, the present invention may also be used in various other applications such as in a gas analysis device employing FTIR spectroscopy for a urea SCR system that is used to reduce NOx contained in exhaust gas, or a gas analysis device employing FTIR spectroscopy for a methanol reforming system for fuel cells, and the like.

Additionally, the gas analysis device 100 according to the present invention is not limited to employing FTIR spectroscopy, and may also be applied to gas analysis devices that quantitatively analyze multiple components contained in a test gas by employing, for example, non-dispersive infrared absorption (NDIR) spectroscopy, quantum cascade laser infrared (QCL-IR) spectroscopy, non-dispersive ultraviolet (NDUV) spectroscopy, and ultraviolet (UVA) spectroscopy.

Second Embodiment

When hydrocarbon compounds having a high boiling point, in other words, hydrocarbon compounds having a high carbon number are analyzed using, for example, FTIR spectroscopy, because the peaks in the absorption spectra thereof appear in substantially the same position, identification becomes extremely difficult.

Figure 6:
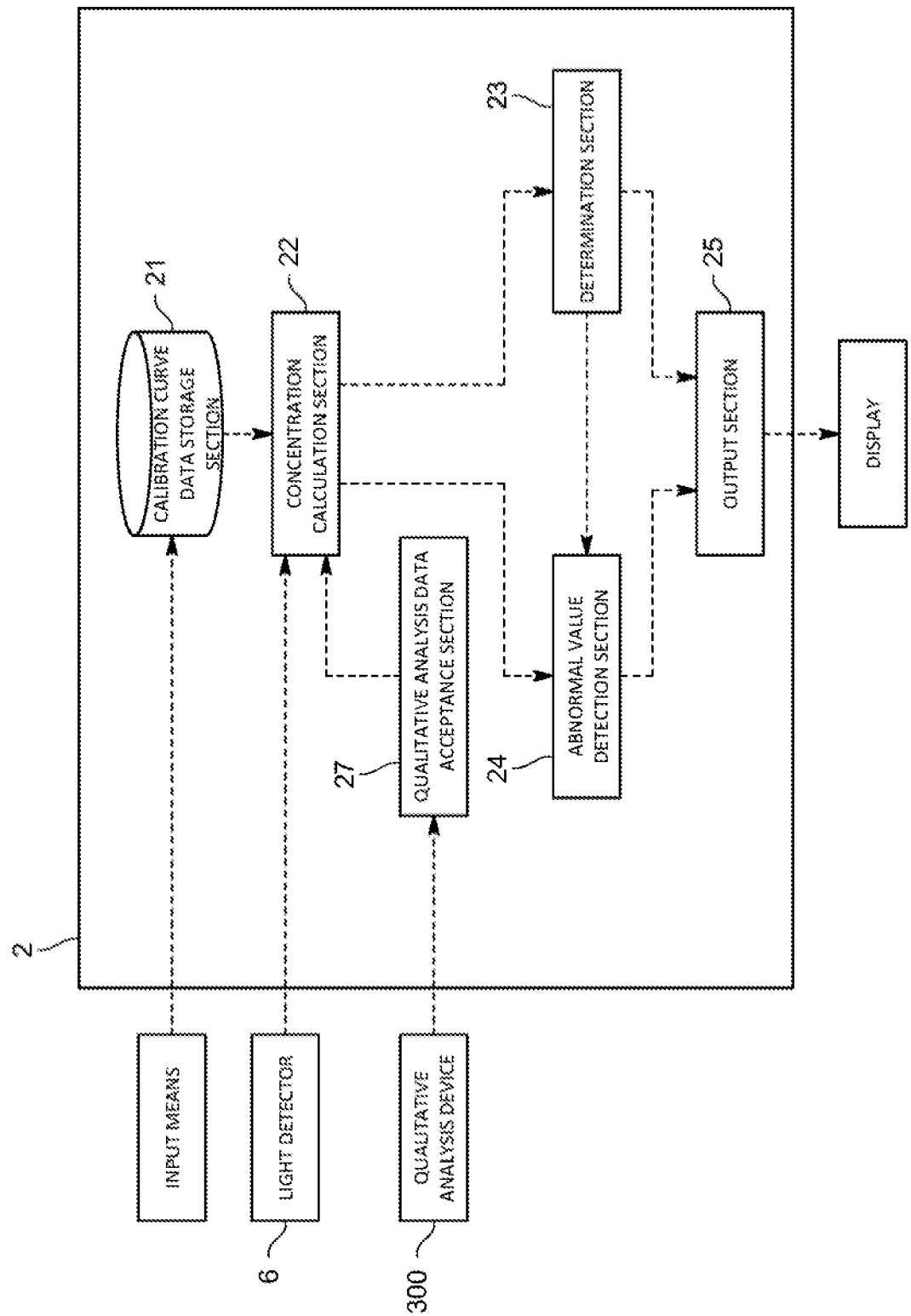
FIG. 6 is a function block diagram showing functions of an information processing device of a second embodiment.

Therefore, as is shown in FIG. 6, it is also possible for the information processing system 2 to be further provided with the functions of a qualitative analysis data acceptance section 27 that receives qualitative analysis data obtained by performing qualitative analysis on a test gas.

Qualitative analysis data is data that shows components contained in a test gas, and is data that is obtained by a qualitative analysis device 300 such as, for example, a mass analyzer that is separate from the gas analysis device 100 of the present embodiment.

Various types of analysis device such as a gas chromatograph mass analyzer, or a quadrupole mass analyzer or the like may be used as the qualitative analysis device 300, however, here, a soft ionization mass analyzer is used. By using a soft ionization mass analyzer, ionization can be performed using a comparatively low amount of energy on hydrocarbon compounds having a high carbon number, aromatic hydrocarbon compounds (PAH), and hydrocarbon compounds such as light oil components, and what is known as fragmentation can be suppressed. As a result, because split peaks are reduced, identification of hydrocarbon compounds becomes comparatively easier.

In the above-described structure, it is preferable that, when the qualitative analysis data indicates that higher boiling compounds are contained in a test gas, the concentration calculation section 22 calculate the concentrations of components to be measured using the first calibration curve data, while when the qualitative analysis data indicates that higher boiling compounds are not contained in a test gas, that the concentration calculation section 22 calculate the concentrations of the components to be measured using the second calibration curve data.

This will now be described more specifically. Prior to the qualitative analysis by the gas analysis device 100 starting, alternatively, after there has been an alteration to the analysis conditions such as to the engine, fuel, or catalyst or the like that are being used, firstly, qualitative analysis is performed on the test gas by the qualitative analysis device 300, and qualitative analysis data showing the results of this qualitative analysis is then received by the qualitative analysis data acceptance section 27.

Next, the concentration calculation section 22 refers to the qualitative analysis data received by the qualitative analysis data acceptance section 27, and determines whether or not any previously stipulated higher boiling compounds are contained in the test gas.

If the concentration calculation section 22 determines that higher boiling compounds are contained in the test gas, then the concentration calculation section 22 calculates concentrations of the components to be measured using the first calibration curve data. At this time, if the concentration calculation section 22 determines that a plurality of types of higher boiling compounds are contained in the test gas, then it extracts from the calibration curve storage unit 21 calibration curve data in which the effects on the concentrations of the components to be measured from the plurality of types of higher boiling compounds have been corrected to serve as the first calibration curve data, and then calculates the concentrations of components to be measured.

On the other hand, if the concentration calculation section 22 determines that higher boiling compounds are not contained in the test gas, then the concentration calculation section 22 calculates the concentrations of the components to be measured using the second calibration curve data.

By employing this type of structure, it is possible to automatically differentiate between when to use the first calibration curve data and when to use the second calibration curve data depending on whether or not higher boiling compounds are contained in a test gas.

Furthermore, even if carbonization compounds having a high carbon number which are difficult to identify using, for example, FTIR spectroscopy are contained in a test gas, because a soft ionization mass analyzer is used as the qualitative analysis device 300, it is comparatively easy to determine whether or not high boiling point carbonization compounds are contained in a test gas. As a result, the gas analysis device 100 is able to automatically determine the most appropriate calibration curve data from the first calibration curve data or the second calibration curve data, and concentrations of components to be measured can be accurately calculated irrespective of whether or not high boiling point carbonization compounds are contained in the test gas.

Note that it is not absolutely essential for the above-described qualitative analysis data to be used when determining whether or not higher boiling compounds are contained in a test gas.

For example, it is also possible for the gas analysis device 100 to be formed such that, if the qualitative analysis data shows that a plurality of types of components are contained in a test gas, then the concentration calculation section 22 acquires from the calibration curve data storage section 21 calibration curve data that corresponds to this plurality of types of components, and calculates the concentrations of the respective components using this calibration curve data.

In addition, the present invention is not limited to the above-described embodiments, and it is to be understood that various modifications and the like are possible insofar as they do not depart from the spirit or scope of the present invention.

INDUSTRIAL APPLICABILITY

According to the present invention, it is possible to reduce measurement errors that are due to the effects of higher boiling compounds, so that an improvement in analysis accuracy is achieved.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. A gas analysis device that analyzes components to be measured that are contained in a test gas using a light spectrum obtained by irradiating light onto the test gas, comprising:
a calibration curve data storage section in which is stored first calibration curve data in which interference effects on concentrations of the components to be measured from higher boiling compounds whose boiling point is higher than a heating temperature of an analyzer into which the test gas has been introduced have been corrected; and
a concentration calculation section that calculates concentrations of components to be measured using the first calibration curve data.

2. The gas analysis device according to claim 1, wherein the calibration curve data storage section additionally stores second calibration curve data in which the interference effects from the higher boiling point compounds have not been corrected, and
when the higher boiling point compounds are not contained in the test gas, the concentration calculation section calculates concentrations of the components to be measured using the second calibration curve data.

3. The gas analysis device according to claim 2, wherein the calibration curve data storage section stores calibration curve data for higher boiling compounds that is used to calculate concentrations of the higher boiling compounds, and
there is further provided a determination section that determines whether or not concentrations of the higher boiling compounds calculated by the concentration calculation section using the higher boiling compound calibration curve data are equal to or less than a predetermined threshold value, and
when the concentrations of the higher boiling compounds are determined by the determination section to be equal to or less than the predetermined threshold value, the concentration calculation section calculates concentrations of the components to be measured using the second calibration curve data.

4. The gas analysis device according to claim 1, wherein there is further provided a qualitative analysis data acceptance section that receives qualitative analysis data obtained as a result of qualitative analysis being performed on the test gas, and
when the qualitative analysis data shows that the higher boiling compounds are contained in the test gas, the concentration calculation section calculates concentrations of the components to be measured using the first calibration curve data.

5. The gas analysis device according to claim 4, wherein when the qualitative analysis data shows that a plurality of types of the higher boiling compounds are contained in the test gas, the concentration calculation section uses calibration curve data in which the interference effects on the concentrations of the components to be measured from the plurality of types of higher boiling compounds have been corrected as the first calibration curve data.

6. The gas analysis device according to claim 1, wherein the higher boiling compounds are alkanes having a carbon number of not less than 10 and not more than 20.

7. The gas analysis device according to claim 1, further comprising:
a cell that contains the test gas; and
a heating unit that heats the cell, wherein
a temperature of the cell that is heated by the heating unit is the heating temperature.

8. A non-transitory storage medium storing a program for a gas analysis device that is used in a gas analysis device that analyzes components to be measured that are contained in a test gas using a light spectrum obtained by irradiating light onto the test gas, and that causes a computer to perform functions of:
a calibration curve data storage section in which is stored first calibration curve data in which interference effects on concentrations of the components to be measured from higher boiling compounds whose boiling point is higher than a heating temperature of an analyzer into which the test gas has been introduced have been corrected; and
a concentration calculation section that calculates concentrations of components to be measured using the first calibration curve data.

9. A gas analysis method in which components to be measured that are contained in a test gas are analyzed using a light spectrum obtained by irradiating light onto the test gas, and has:
a calibration curve data storage step in which first calibration curve data in which interference effects on concentrations of the components to be measured from higher boiling compounds whose boiling point is higher than a heating temperature of an analyzer into which the test gas has been introduced have been corrected is stored; and
a concentration calculation step in which concentrations of components to be measured are calculated using the first calibration curve data.

* * * * *